(12) United States Patent
Lizotte (10) Patent No.: US 11,389,307 B2
(45) Date of Patent: Jul. 19, 2022

(54) FLEXIBLE PROSTHETIC COVER

(71) Applicant: FUSION LIMB SYSTEMS, LLC, Tacoma, WA (US)

(72) Inventor: Thomas Lizotte, Tacoma, WA (US)

(73) Assignee: Fusion Limb Systems, LLC, Tacoma, WA (US)

( * ) Notice: Subject to any disclaimer, the term of this patent is extended or adjusted under 35 U.S.C. 154(b) by 0 days.

(21) Appl. No.: 17/050,629

(22) PCT Filed: Apr. 24, 2019

(86) PCT No.: PCT/US2019/028964
§ 371 (c)(1),
(2) Date: Oct. 26, 2020

(87) PCT Pub. No.: WO2019/209980
PCT Pub. Date: Oct. 31, 2019

(65) Prior Publication Data
US 2021/0307941 A1    Oct. 7, 2021

Related U.S. Application Data (60) Provisional application No. 62/663,094, filed on Apr. 26, 2018.

(51) Int. Cl.
*A61F 2/60* (2006.01)
*A61F 2/78* (2006.01)
(Continued)

(52) U.S. Cl.
CPC .............. *A61F 2/7812* (2013.01); *A61F 2/80* (2013.01); *A61F 2002/5003* (2013.01); *A61F 2002/5089* (2013.01); *A61F 2002/7837* (2013.01)

(58) Field of Classification Search
CPC .. A61F 2/7812; A61F 2/80; A61F 2/60; A61F 2002/5089; A61F 2002/5001
See application file for complete search history.

(56) References Cited

U.S. PATENT DOCUMENTS

| 4,938,775 A | * | 7/1990 | Morgan | A61F 2/60 623/27 |
| 5,755,812 A | * | 5/1998 | Becker | A61F 2/76 623/33 |

(Continued)

FOREIGN PATENT DOCUMENTS

| WO | 2002/028163 A2 | 4/2002 |
| WO | 2018/065218 A1 | 4/2018 |

OTHER PUBLICATIONS

Nader et al., "Otto Bock Prothesen-Kompendium Prothesen fur die untere Extremitat 3. uberarbeitete und erweiterte Auflage", Schiele & Schon, XP055OO6790, Jan. 1, 2000, 127 pages.

(Continued)

*Primary Examiner* — Bruce E Snow
(74) *Attorney, Agent, or Firm* — Kilpatrick Townsend & Stockton LLP (57) ABSTRACT

A prosthetic cover (104) for a prosthetic support element (102) can include a substantially cylindrical hollow body (106) with a first end and a second end and sized to fit around a support element of a prosthesis. A first flexible end seal (108) and a second flexible end seal (110) can each attach with the substantially cylindrical hollow body at the first and second ends, respectively, and connect the hollow body with the support element of the prosthesis by deforming about the support element when the prosthetic cover is installed around the support element.

19 Claims, 8 Drawing Sheets

(51) Int. Cl.
*A61F 2/80* (2006.01)
*A61F 2/50* (2006.01)

(56) References Cited

U.S. PATENT DOCUMENTS

| | | | | |
|---|---|---|---|---|
| 7,169,189 | B2* | 1/2007 | Bjarnason | A61F 2/7812 |
| | | | | 602/26 |
| 9,192,486 | B2* | 11/2015 | Rauch | A61F 2/78 |
| 9,539,119 | B2* | 1/2017 | Sauer | A61F 2/78 |
| 2007/0162154 | A1 | 7/2007 | Scott | |

OTHER PUBLICATIONS

Application No. PCT/US2019/028964, International Search Report and Written Opinion, dated Oct. 16, 2019, 15 pages.

* cited by examiner

FLEXIBLE PROSTHETIC COVER

BACKGROUND

Typical prostheses include a socket, a contact element such as an artificial foot, blade, or pod, and a structural frame optionally including joints and shock absorptive elements connecting the two. Most designs can be categorized as exoskeletal or endoskeletal prostheses. In an exoskeletal prosthesis, support is derived from an external frame often approximating the shape of a limb. These designs can be very strong and cosmetically approximate a lost limb, but are also heavier and more limited in terms of adjustability, replacement, and repair. Endoskeletal prosthesis derive support from an internal frame that does not necessarily approximate natural physiology, and thus are typically lightweight and simpler to modify, adjust, and repair. However, the structural features of endoskeletal prosthesis can snag on skin or clothing and are often visually apparent even when concealed by clothing. Commercially available coverings for endoskeletal prostheses can completely obviate the original cost, weight, and adjustability advantages of the chosen prosthetic design. Thus, a present need exists for improved prosthetic coverings that can be custom fitted, visually appealing, highly dynamic/functional, lightweight, economical, and readily applied to a wide variety of prostheses

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with at least one embodiment of the present disclosure, a flexible prosthetic cover is disclosed. The flexible prosthetic cover includes a substantially cylindrical hollow body with two ends that is sized to fit around a support element of a prosthesis. The prosthetic cover includes two flexible end seals that connect with the hollow body at each end and connect the body with the underlying support element. The connection is typically fluid-tight, or at least resistant to liquid infiltration. Each end seal is formed of a flexible and elastic material, such as silicone, that can deform to allow insertion of the load-bearing element through the prosthetic cover and end seals and to securely attach the prosthetic cover at any desired position along the load-bearing element.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
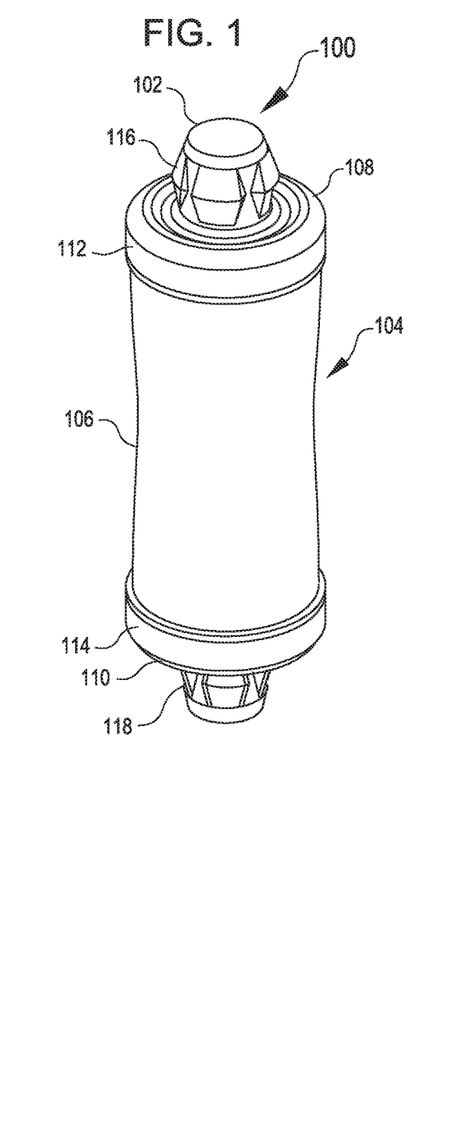
FIG. 1 is a perspective view showing an assembly of a flexible prosthetic cover attached with a prosthetic structural pylon.

Referring now to the drawings, in which like reference numerals represent like parts throughout the several views, FIG. 1 shows an assembly 100 of a flexible prosthetic cover 104 attached with a prosthetic structural element 102, such as a structural pylon, in accordance with at least one embodiment of the present disclosure. Although the structural element 102 is represented as a cylindrical pylon throughout this disclosure, it will be understood that the prosthetic covers described can readily fit around and protect many forms of structural elements with widely varying degrees of complexity.

The prosthetic cover 104 includes a flexible, substantially cylindrical hollow body 106. This hollow body 106 can have a variety of specific shapes, including a basic cylindrical shape, a narrowing, hour-glass shape to any suitable degree (as shown), or more complex shapes. The hollow body 106 is sized to accommodate the structural element 102 therein. Each end of the hollow body 106 is capped with first and second flexible end seals 108, 110. In some embodiments, the end seals 108, 110 form a liquid-tight seal with the hollow body 106, and may also provide a liquid-tight seal with support element 102 when the protective cover 104 is installed. The end seals can include any suitably strong and flexible material, such as but not limited to silicone and other flexible polymers. In some embodiments, the end seals can be shaped to accommodate flexure, e.g., with a curved or wavy cross section. In some cases, the end seal can form a seal against a variety of arbitrary shapes, including the structural element or pylon, a foot or similar attachment, a socket, or other component that the end seal contacts.

Figure 2:
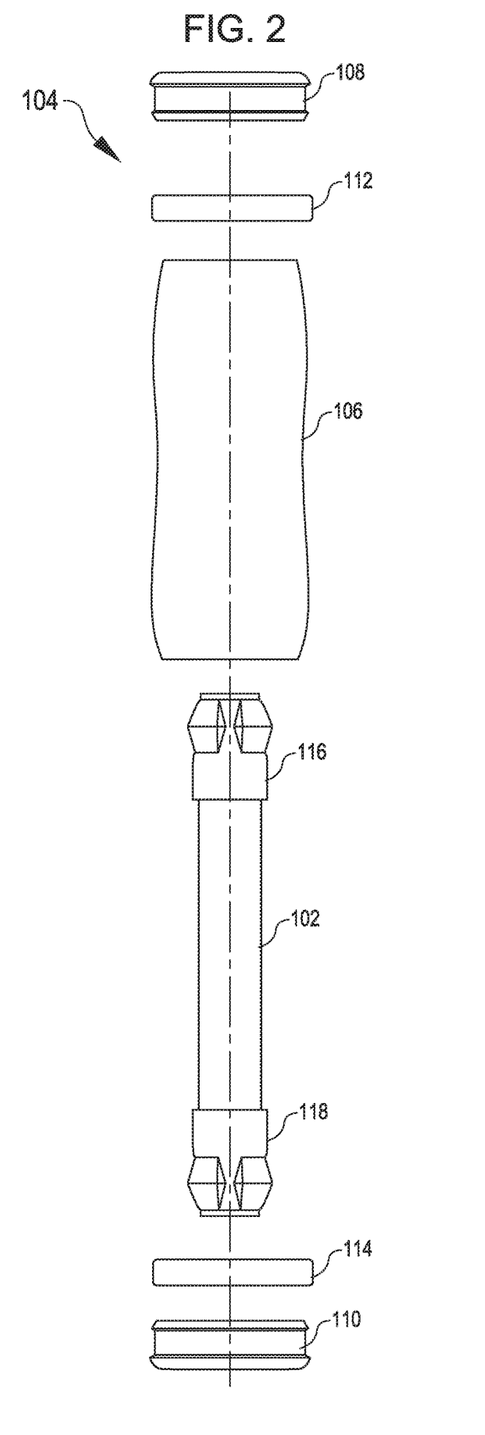
FIG. 2 is an exploded side elevation view showing the flexible prosthetic cover of FIG. 1.

The end seals 108, 110 can be secured to the protective cover by way of, e.g., locking bands or other suitable retainers 112, 114 that bias the end seals 108, 110 against the hollow body 106. The position of the prosthetic cover 104 along the structural element 102 can be secured by way of, e.g. clamps 116, 118 (e.g. locking collars or tube clamps) that can removably attach with the structural element 102 and prevent the cover 104 from sliding thereon. FIG. 2 is an exploded side elevation view showing the prosthetic cover 104 of FIG. 1, and better illustrating the individual components thereof. According to some embodiments, the end seals 108, 110 may form a secure attachment with the hollow body 106 without the inclusion of the locking bands. Similarly, in some embodiments the claims 116, 118 may also be optional, i.e. with the end seals 108, 110 being sufficiently tight or otherwise connected or adhered to the pylon 102. The end seals 108, 110 are preferably removably connected with the pylon 102 when assembled.

The prosthetic cover 104 of FIGS. 1-2 is formed in a roughly symmetrical, hour-glass shape that can mimic the natural shape of a limb from beneath clothing, or can be aesthetically pleasing if exposed. The form of the cover 104 is also suitable for providing protection from any otherwise exposed edges or components of the structural element 102 when installed, i.e. for preventing snags on clothing or preventing injuries to the skin of the opposite sound limb.

Figure 3:
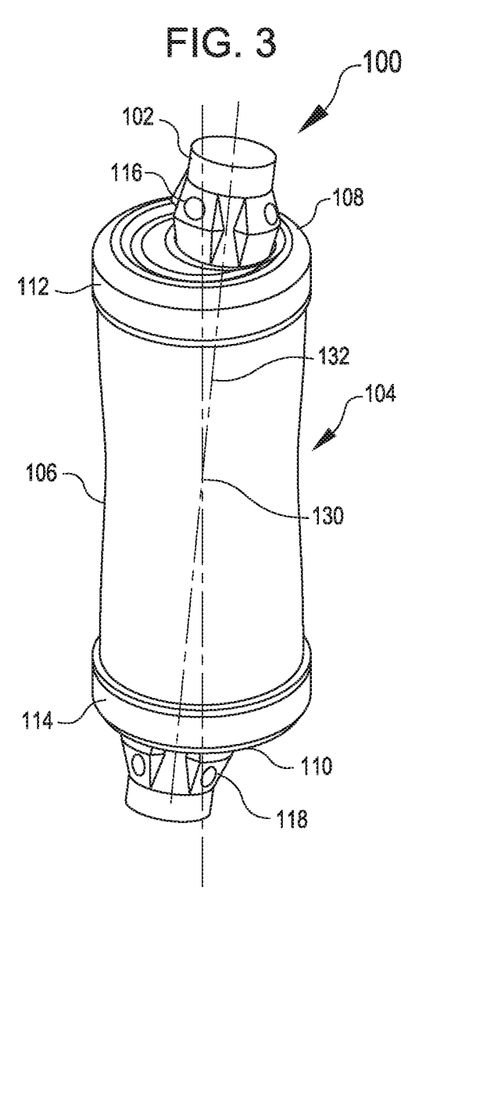
FIG. 3 is a perspective view illustrating the angular and torsional flexibility of the flexible prosthetic cover of FIGS. 1-2 attached with the prosthetic structural pylon.

FIG. 3 is a perspective view illustrating the angular and torsional flexibility of the flexible prosthetic cover 104 of FIGS. 1-2 attached with the prosthetic structural pylon 102, in accordance with at least one embodiment of the present disclosure. As shown, the prosthetic cover 104 can move extensively relative to the pylon 102 while installed thereon due to the flexibility and shape of the end seals 108, 110. For example, when the pylon 102 is tilted relative to the cover 104, the end seals 108, 110 can deform without unsealing from the pylon, allowing the pylon centerline 132 and cover centerline 130 to diverge. The elasticity of the end seals 108, 110 will tend to bring the cover 104 back to center when not under load. Similarly, the elasticity of the end seals 108, 110 will allow the cover to partially rotate around the pylon 102 without releasing the pylon, or to move a small distance up and down along the pylon. The cover 104 can therefore tilt, translate, or rotate elastically around the pylon 102, allowing the cover to be readily moved out of the way when work is done on the underlying prosthesis, while adjusting clothing or shoes around the prosthesis, while walking, bending, or turning, or any other task which might be obstructed by a more rigid, conventional prosthetic cover.

Figure 4:
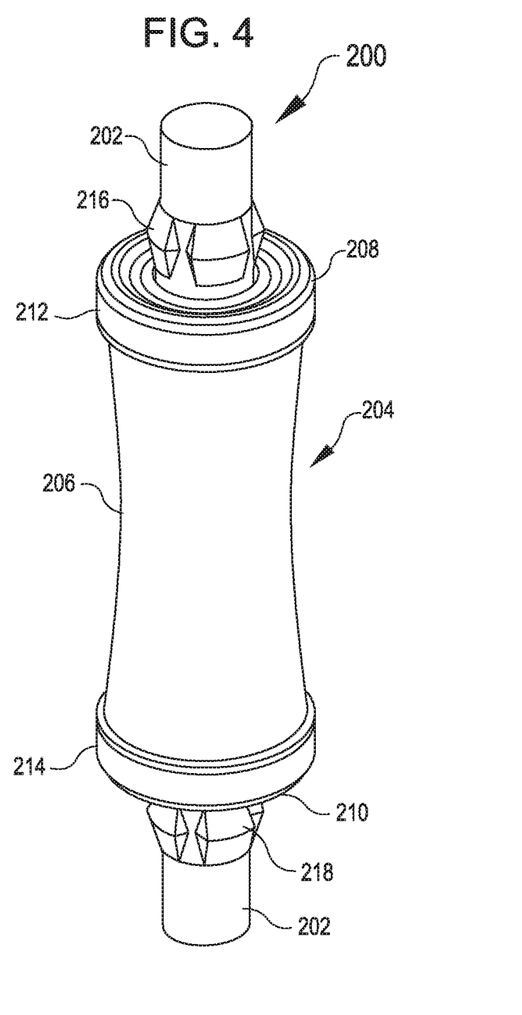
FIG. 4 is a perspective view showing a second embodiment of an assembly of a flexible prosthetic cover attached with a prosthetic structural pylon.

FIG. 4 is a perspective view showing a second embodiment of an assembly 200 of a similar flexible prosthetic cover 204 attached with a prosthetic structural pylon 202, in accordance with at least one embodiment of the present disclosure. This second example of a prosthetic cover 204 illustrates a narrower, low-profile shape of the hollow body 206 when compared to the hollow body 106 of the prosthetic cover 104 shown in FIGS. 1-3.

The hollow body 206 can also have a variety of specific shapes, including a basic cylindrical shape, a narrowing, hour-glass shape to any suitable degree (as shown), or more complex shapes. The hollow body 206 is sized to accommodate the structural element 202 therein. Each end of the hollow body 206 is capped with first and second flexible end seals 208, 210. In some embodiments, the end seals 208, 210 form a liquid-tight seal with the hollow body 206, and may also provide a liquid-tight seal with support element 202 when the protective cover 204 is installed. The end seals can include any suitably strong and flexible material, such as but not limited to silicone and other flexible polymers. In some embodiments, the end seals can be shaped to accommodate flexure, e.g., with a curved or wavy cross section.

Figure 5:
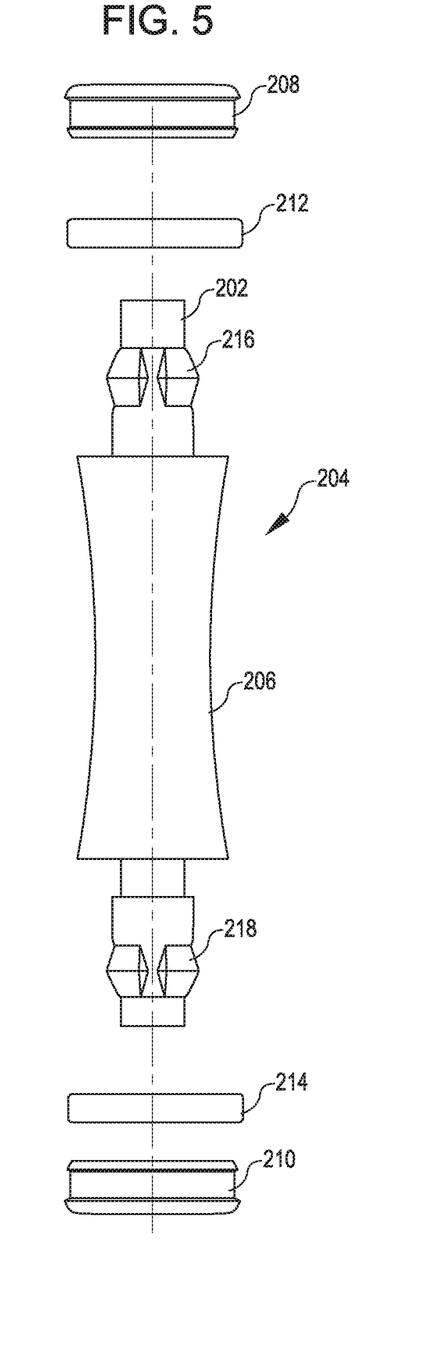
FIG. 5 is an exploded side elevation view showing the flexible prosthetic cover of FIG. 4.

The end seals 208, 210 can be secured to the protective cover by way of, e.g., locking bands or other suitable retainers 212, 214 that bias the end seals 208, 210 against the hollow body 206. The position of the prosthetic cover 204 along the structural element 202 can be secured by way of, e.g. clamps 216, 218 that can removably attach with the structural element 202 and prevent the cover 204 from sliding thereon. FIG. 5 is an exploded side elevation view showing the prosthetic cover 204 of FIG. 4, and better illustrating the individual components thereof.

Figure 6:
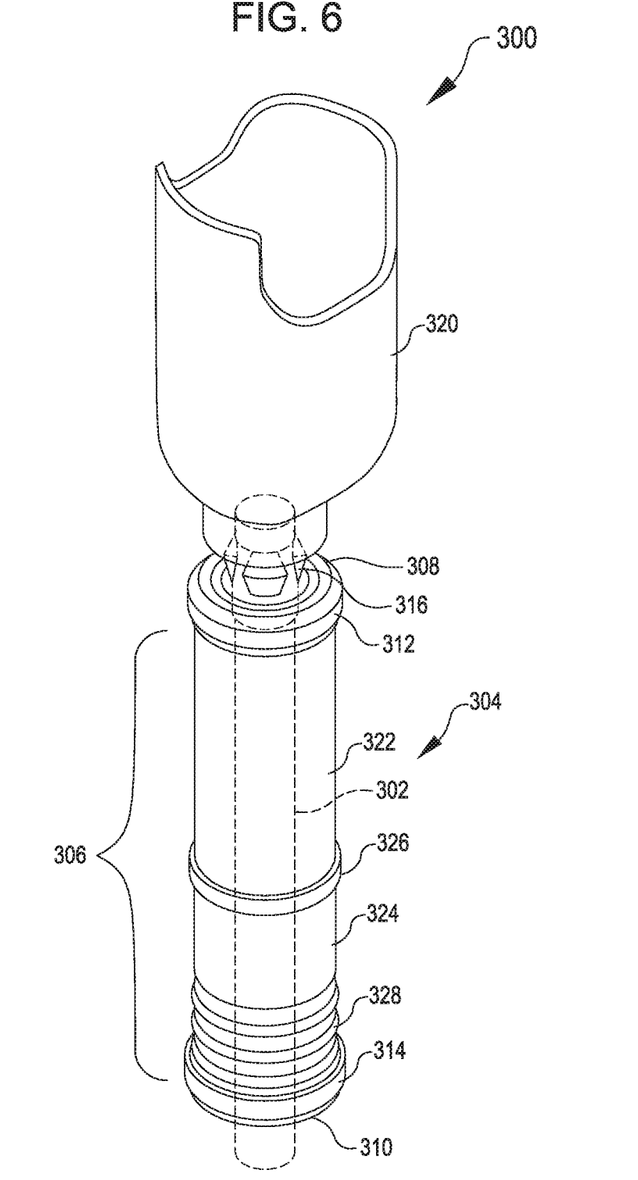
FIG. 6 is a perspective view showing a third embodiment of an assembly of a flexible prosthetic cover attached with a prosthetic structural pylon, a socket, and a foot.

FIG. 6 is a perspective view showing a third embodiment of an assembly 300 of a flexible prosthetic cover 304 attached with a prosthetic structural pylon 302 and a socket 320, in accordance with at least one embodiment of the present disclosure. This third example of a flexible prosthetic cover 304 includes a variable-length hollow body 306 that can be extended or contracted to cover an internal structural element 302 of any suitable length.

Prosthetic cover 304 includes similar features to those of covers 104, 204 described above, including a hollow body 306 sized to accommodate the structural element 302 therein, capped with first and second flexible end seals 308, 310. In some embodiments, the end seals 308, 310 form a liquid-tight seal with the hollow body 306, and may also provide a liquid-tight seal with support element 302 when the protective cover 304 is installed. The end seals can include any suitably strong and flexible material, such as but not limited to silicone and other flexible polymers. In some embodiments, the end seals can be shaped to accommodate flexure, e.g., with a curved or wavy cross section.

The end seals 308, 310 can be secured to the protective cover 304 by way of locking bands or other suitable retainers 312, 314 that bias the end seals 308, 310 against the hollow body 306. The position of the prosthetic cover 304 along the structural element 302 can be secured by way of, e.g. clamps 316, 318 that can removably attach with the structural element 302 and prevent the cover 304 from sliding thereon.

Figure 7:
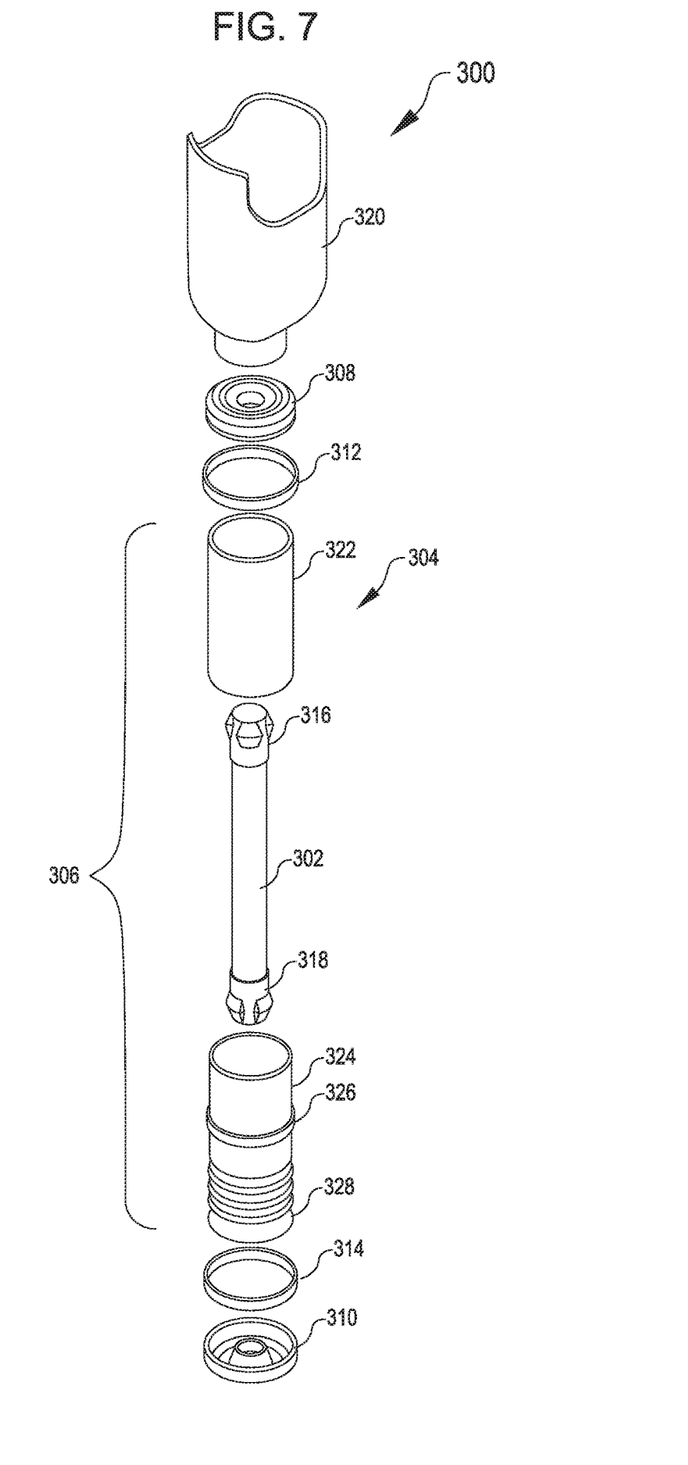
FIG. 7 is an exploded side elevation view showing the flexible prosthetic cover of FIG. 6.

In accordance with at least one embodiment of the present disclosure, prosthetic cover 304 has a multi-part hollow body 306 formed of at least two portions, shown here as an upper body portion 322 and a lower body portion 324 that are coupled together by way of a sliding fit and optionally a third locking band or retainer 326. The sliding fit between the upper and lower body portions 322, 324 of the hollow body allow a user to change the length of the hollow body 306 by sliding the coupled upper and lower body portions together or apart. In some embodiments, one or both of the upper and lower body portions 322, 324 can include a gasket, O-ring, or similar feature where they engage with each other to seal the portions together and/or prevent liquid entry. Alternatively, an O-ring, band, or similar structure can be included with or formed to the third locking band or retainer 326. In some embodiments, a shaped surface 328 can be formed into one or more of the portions of a multi-part hollow body 306 for aesthetic purposes, to provide a gripping surface, or to enhance the structural properties thereof. For example, the shaped surface 328 can include a ribbed or wavy shape that permits limited longitudinal deformation. FIG. 7 is an exploded side elevation view showing the prosthetic cover 304 of FIG. 6, and better illustrating the individual components thereof.

Figure 8:
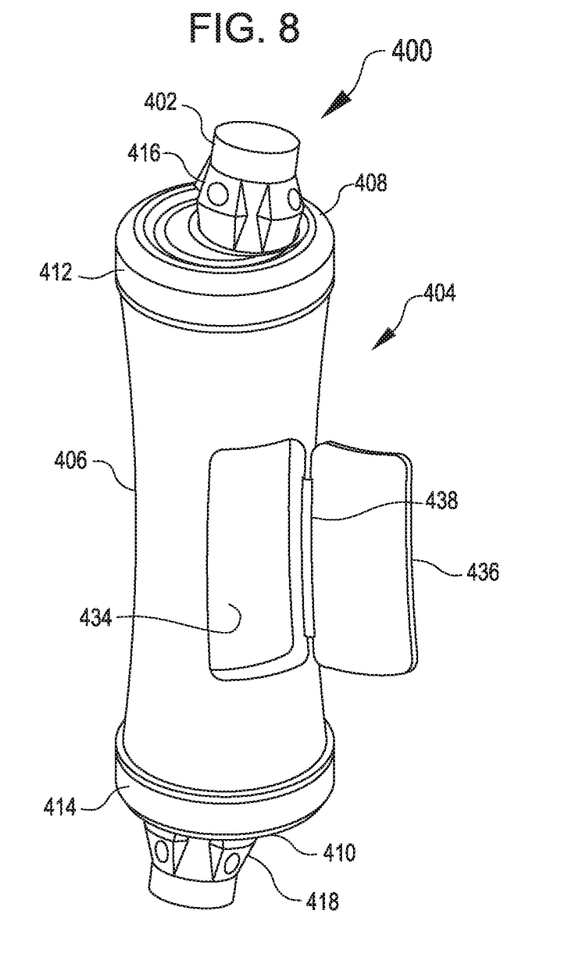
FIG. 8 is a perspective view showing a fourth embodiment of an assembly of a flexible prosthetic cover including pocket enclosure.

FIG. 8 is a fourth example of an assembly 400 of a flexible prosthetic cover 404 attached with a prosthetic structural element 402, such as a structural pylon, in accordance with at least one embodiment of the present disclosure, and similar to the embodiments shown above with reference to FIGS. 1-7. The prosthetic cover 404 similarly includes a flexible, substantially cylindrical hollow body 406 sized to accommodate the structural element 402 therein. Each end of the hollow body 406 is capped with first and second flexible end seals 408, 410, as well as retaining clamps 416, 418 and optional retainers 412, 414.

In accordance with at least one embodiment of the present disclosure, flexible prosthetic cover 404 can further include a pocket enclosure 434, which can be configured as a trap-door pocket for discreetly containing items. For example, in some embodiments, the pocket enclosure 434 is configured for containing items such as insulin or other medication, for containing credit cards, car keys, or other small items, or the like. In some embodiments, the pocket enclosure 434 can also include retention elements (not shown) for assisting in the securement and retention of small items, such as elastic straps, pockets, or the like. The pocket enclosure 434 is preferably constructed as a pocket within the mold (i.e. injection mold) that forms the hollow body 406, thus preserving the water-tight sealed compartment formed by the hollow body around the pylon 402 when the cover 404 is assembled. The pocket enclosure 434 can further include an external closure or trap door 436, with a hinge element 438 enabling the pocket enclosure to close, producing a discretely smooth outer surface and protecting items stored within. In some embodiments, the pocket enclosure 434 is also configured to seal, e.g. by way of a gasket or otherwise sealed closure, to define an independently watertight, sealed enclosure.

The prosthetic covers described herein can be used in a universal, symmetrical prosthetic covering system suitable for almost every type of amputee and capable of covering most types of lower extremity prostheses currently available. Such prosthetic covers can be readily applied in the clinic to most prostheses upon delivery of new prostheses and with minimal adjustment. At least some embodiments are suitable for application to endoskeletal prostheses and for covering and protect components between the foot and the socket. Unlike most conventional prosthetic covers, the embodiments herein described are specifically designed to cover the typically exposed componentry of modern lower extremity endoskeletal prostheses and improve the appearance of today's high-tech prostheses.

Figure 9:
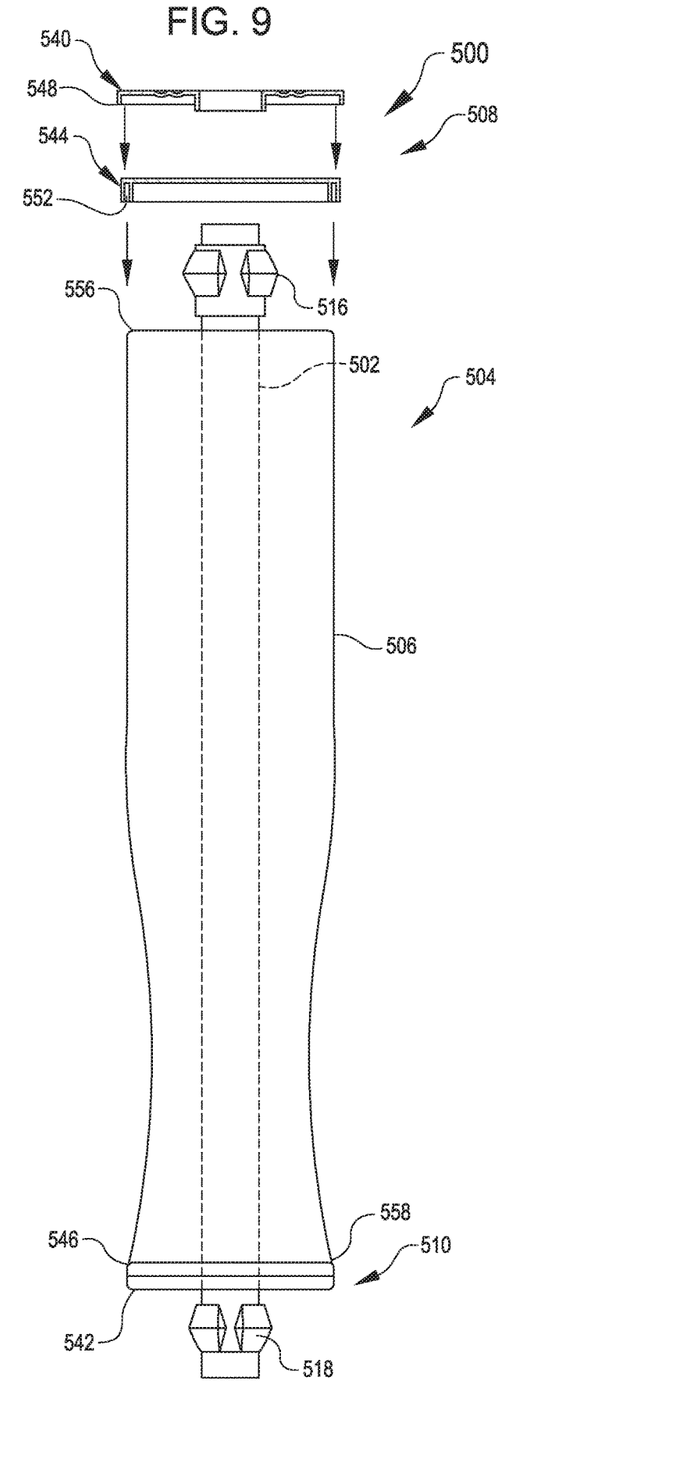
FIG. 9 is a side elevation view showing a fifth embodiment of an assembly of a flexible prosthetic cover.

FIG. 9 is a fourth example of an assembly 500 of a flexible prosthetic cover 504 attached with a prosthetic structural element 502, such as a structural pylon, in accordance with at least one embodiment of the present disclosure, and similar to the embodiments shown above with reference to FIGS. 1-8. The prosthetic cover 504 similarly includes a flexible, substantially cylindrical hollow body 506 sized to accommodate the structural element 502 therein. Each end of the hollow body 506 is capped with first and second flexible end seals 508, 510. In contrast with the end seals 108, 110 shown in FIG. 1, each of the end seals 508, 510 of flexible prosthetic cover 504 can include a two-part assembly of an end cap 540, 542 that connects to and partially encloses a sealing ring 544, 546. The hollow body 506 shown is a partial hourglass shape, but it will be understood that a variety of specific prosthetic cover shapes can be used.

The assembly of end caps 540, 542 and sealing rings 544, 546 can replace previously discussed assemblies of flexible end seals (e.g. 108, 110) and optional retainers (112, 114). According to some embodiments, the end seals 508, 510 can attach to the substantially cylindrical hollow body 506 by a snap-fit connection by which the end seals elastically deform to firmly attach to the upper edge 556 and lower edge 558 of the hollow body. In some embodiments, the end caps 540, 542 can be permanently or semi-permanently connected with the sealing rings 544, 546, e.g. by way of adhesive or similar means. The end caps 540, 542 can be formed of any suitable flexible or semi-flexible plastic, e.g. HDPE or silicone. The end seals 508, 510 are sufficiently flexible to permit the end seals to receive and retain the structural element 502, and to accommodate limited motion of the structural element within the hollow body 506, without unseating from the hollow body. In some embodiments, the end caps 540, 542 can have a rippled or textured shape to decrease the effective stiffness of the end caps and improve their ability to deform under load. The assembly of the structural element 502, end seals 508, 510, and hollow body 506 is preferably watertight or at least resistant to water intrusion.

Figure 10:
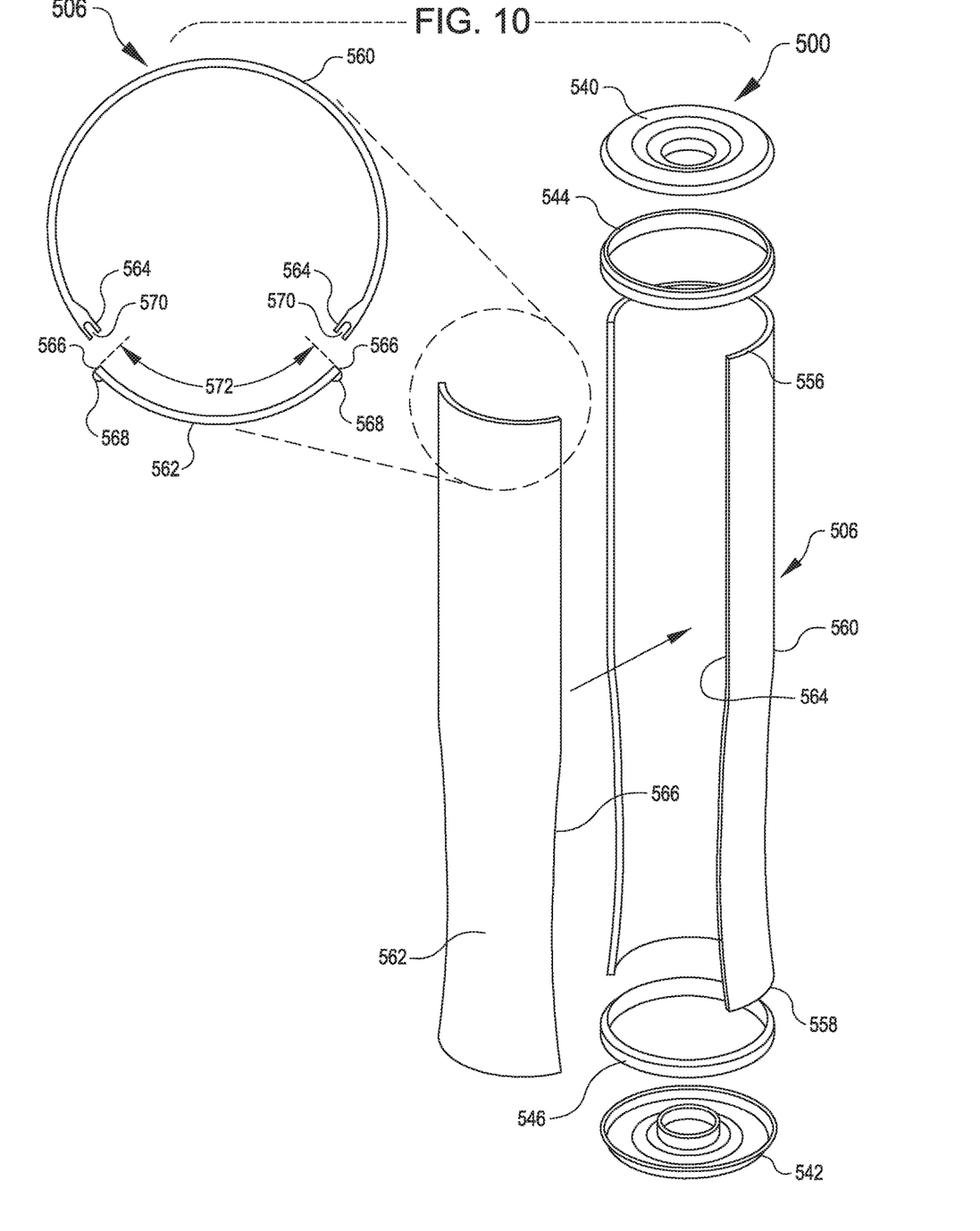
FIG. 10 is an exploded perspective view showing the assembly of the flexible prosthetic cover of FIG. 9.

In accordance with at least one embodiment of the present disclosure, the flexible prosthetic cover 504 can include a removable panel 562, as shown in FIG. 10. FIG. 10 is an exploded perspective view showing the flexible prosthetic cover 504 in a disassembled state, with particular attention to the assembly of the substantially cylindrical hollow body 506 from a first, main body 560 and removable panel 562 that can connect with and be removed from the main body in a lateral direction with respect to the main body. The main body 560 includes two receiving edges 564 that can receive insertion edges 566 of the removable panel 562. In some specific embodiments, each receiving edge 564 is an opening or track into which the matching insertion edge 566 can be placed in a snap fit. A first arc 570 that defines the receiving edges 564 of the main body 560 is approximately equal in size to a second arc 572 that defines the insertion edges 566, though in some embodiments the second art 572 may be slightly longer to account for overlap. According to various embodiments, the main body 560 can connect with the removable panel 562 by way of a lap joint or other suitable connective feature, or may be connected by way of adhesive, by connectors such as clips, screws, bolts, or the like, or any other suitable connector. The insertion edge 566 can further include a gasket element 568 that, when the insertion edge 566 is connected with the receiving edge 564, seals main body 560 and removable panel 562 together. The main body 560 and removable panel 562 can preferably connect to form a watertight seal, and can be assembled with the end seals 508, 510 to form a water-tight assembly when connected with the structural member 502. In some embodiments, the end seals 508, 510 can provide additional support for maintaining the connection between the main body 560 and removable panel 562.

According to some embodiments, the prosthesis cover is rotationally symmetrical, and therefore has a consistent appearance from every angle. The shape of the cover (and particularly the hollow body) can approximate the ankle and shin shape and contour to provide a natural profile when the ankle is exposed, in contrast to the typical sharp angles and componentry visible in contemporary prostheses. In addition, the hollow body (106, 206, 306) can be available in multiple profiles to choose from depending on the patient's preference and size. Similarly, the hollow body of the cover can be formed in a variety of styles and colors, including vibrant translucent colors that amputees may choose from to either complement their prostheses or add a colorful component that disguises typically exposed componentry.

The prosthetic covers described herein are extremely durable. In some embodiments, the hollow body can be formed of a high-strength polymer such as TRITAN plastic (Eastman, Fla., USA) that resists puncturing, warp, cracking, or denting. In some embodiments, the hollow body can be formed of UV resistant material that is highly resilient against fading or deterioration in direct sunlight.

The flexible fit provided by the end seals (e.g. end seals 108, 110) cause the prosthetic cover to be silent in use, so there is no unwanted noise. Primarily, the end seals connect the hollow body of the prosthetic cover to the underlying componentry. In one embodiment, the end seals are made using medical grade, highly durable silicone rubber that provides a seal against elemental intrusion (e.g., rain dirt and mud) while also dampening vibration. The seals can securely attach the prosthesis cover to the prosthesis without additional straps, buckles, glue, or magnets.

The simplicity and lightweight design of the prosthetic covers described herein promote durability. For example, in at least one embodiment, a prosthetic cover including a one piece, substantially tubular hollow body two end or transition seals weighs between 125-145 grams (about 4.5 and 5 ounces, or about ⅕ the weight of 3-D printed covers available).

Importantly, the prosthetic covers as described herein protect the amputee from injury. Many amputees who wear prostheses are dysvascular and/or diabetic and are therefore at high risk for abrasion or puncture injuries to the sound limb. By containing or otherwise extending beyond the extend of the sharp edges, nuts and bolts in the underlying structural elements of the prosthesis, an installed prosthetic cover as described can prevent unwanted contact between such components and the opposite limb of a wearer.

Prosthetic covers as described herein can also be installed with a wide variety of commercially available prosthetics, including but not limited to: high motion feet systems, shock absorbers, torsion units, and vacuum systems. In addition, modifications can be made for accommodating vacuum tubes (i.e. for vacuum-type prostheses) through the end seals and/or through the hollow body. This flexibility of use is due in part to the dynamics of the transition or end seals at each end of the prosthetic covers. The end seals connect the prosthetic cover with the underlying componentry while also providing shock absorption and torsion tolerance within the prosthetic system, so that the prosthetic cover will not dampen or impede motion of the prosthetic components in any way.

Installation of a prosthetic cover as described herein can be performed by adapting the end seals to accommodate the diameter of the structural element to which the cover is to be installed, and then simply sliding the assembled cover over the element. Adjustments to the prosthesis can be readily made by simply sliding the prosthetic cover aside to access underlying adjustment screws for necessary alignment changes. The prosthetic covers can be applied universally to almost any type of prosthesis, including both AK's (above knees) and BK's (below knees). The prosthetic covers are suitable for K1-K4 patients, and can be easily customized, e.g. by painting, water dipping or vinyl wrapping with graphics.

In one example of an installation procedure, a prosthetic cover as described above can be installed in five steps. First, the distance between the socket and the foot shell is measured (i.e. the area of exposed underlying endoskeletal componentry to be covered). Let X represent this distance. A small distance, e.g. about 15 mm, is subtracted from this distance to allow for movement of the cover itself. The hollow body can then be reduced from an initial length to this reduced length, e.g. by way of a grinder or comparable tool. Next, the exposed edges of the hollow body should be buffed to remove any sharp edges or burring, and the end seals attached.

The prosthesis should also be prepared for installation by at least partial disassembly, e.g., by removing any large components from the ends of the underlying endoskeletal componentry or structural elements. Once the end seals are attached, the assembly can be slid onto the structural element of the prosthesis. Alcohol can be used as a temporary lubricant for attaching the assembly and prosthesis. The seal and hollow body should be moved as far along the structural element as possible to ensure that inner silicone opening is lying flat on component to ensure a seal. Once in place, the retention elements can be attached to the end seals to firmly connect the end seals with the hollow body of the prosthetic cover down over components pull outer silicone seal over outside of cover. Finally, any detached portions of the prosthesis (e.g., the socket, foot, etc.) can be reinstalled at the ends of the structural element.

When installed, the prosthetic cover should be able to freely move in rotation and vertically, or "float" on the underlying componentry, without interference with any moving parts while the patient is walking or moving. In special circumstances, access may be required to the portion of the structural elements covered by the prosthetic cover in order to adjust or reattach elements of the prosthesis. In such cases, the prosthetic cover can be modified by simply drilling a hole into the hollow body for access, and subsequently using a plug to seal off hole once complete. In such cases, it is typically necessary to only drill one hole, as the prosthetic cover can be rotated to access underlying screws.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. By way of some non-limiting examples, the specific shapes described for the various substantially cylindrical hollow bodies of the prosthetic covers disclosed herein (e.g., straight cylinders, hourglass or partial hourglass shapes, bulbous shapes, multi-part hollow bodies, or shaped surfaces) may be combined with any herein described embodiments of end seals, secondary features (e.g., pocket door 436, FIG. 8), and/or attachments (e.g. prosthetic socket 320).

All references, including publications, patent applications, and patents, cited herein are hereby incorporated by reference to the same extent as if each reference were individually and specifically indicated to be incorporated by reference and were set forth in its entirety herein.

In the following, further examples are described to facilitate understanding of the disclosure:

Example A. A prosthetic cover for a prosthetic support element, the prosthetic cover comprising: a hollow body with a first end and a second end, the hollow body sized to fit around a support element of a prosthesis; a first flexible end seal configured to attach with the hollow body at the first end, and further comprising a first flexible opening therethrough that is sized to receive the prosthetic support element; and a second flexible end seal configured to attach with the hollow body at the second end and further comprising a second flexible opening therethrough that is sized to receive the prosthetic support element, wherein each of the first and second flexible end seals is configured to connect the prosthetic cover with the prosthetic support element by deforming about the prosthetic support element when the prosthetic cover is installed around the prosthetic support element.

Example B: The prosthetic cover of Example A, wherein each one of the first flexible end seal and second flexible end seal forms a respective fluid-tight connection between the hollow body and the support element when the prosthetic cover is installed around the support element.

Example C. The prosthetic cover of any of the preceding examples, wherein the hollow body comprises a polymer shell having at least one of a substantially cylindrical shape, hourglass shape, or bulbous shape.

Example D. The prosthetic cover of any of the preceding examples, wherein the hollow body comprises a ribbed or wavy shape that is operable to allow the hollow body to deform longitudinally.

Example E. The prosthetic cover of any of the preceding examples, wherein the hollow body comprises a main body and a removable panel that is removably connected with the main body in a lateral direction with respect to the main body.

Example F. The prosthetic cover of any of Examples A-D, wherein the hollow body comprises an upper body portion and a lower body portion connected with the upper body portion by a sliding fit configured to allow the hollow body to vary in length.

Example G. The prosthetic cover of any of the preceding examples, further comprising a pocket enclosure defined in an external surface of the hollow body and an external closure configured to enclose the pocket enclosure that can be opened and closed by a user.

Example H. The prosthetic cover of any of the preceding examples, wherein each one of the first flexible end seal and second flexible end seal comprises a flexible silicone.

Example I. The prosthetic cover of any of the preceding examples, further comprising: a first locking band encircling the first flexible end seal and positioned to secure the first flexible end seal to the hollow body; and a second locking band encircling the second flexible end seal and positioned to secure the second flexible end seal to the hollow body.

Example J. The prosthetic cover of any of Examples A-H, wherein: the first flexible end seal comprises a substantially ring-shaped first flexible gasket element connected with the first end of the hollow body, and a first end cap connected to the first flexible gasket element and configured to press the first flexible gasket element onto the first end of the hollow body; and the second flexible end seal comprises a substantially ring-shaped second flexible gasket element connected with the second end of the hollow body, and a second end cap connected to the second flexible gasket element and configured to press the second flexible gasket element onto the second end of the hollow body.

Example K. The prosthetic cover of any of the preceding examples, wherein the prosthetic cover is rotationally symmetrical.

Example L. The prosthetic cover of any of the preceding examples, wherein the hollow body comprises a UV-resistant material.

Example M. The prosthetic cover of any of the preceding examples, wherein the first flexible end seal and the second flexible end seal comprise a vibration dampening material.

Example N. The prosthetic cover of any of the preceding examples, wherein: the first flexible end seal and the second flexible end seal are connected with the hollow body by a watertight seal; and the first flexible end seal and the second flexible end seal are configured to form a watertight seal with the prosthetic support element when the prosthetic cover is installed around the prosthetic support element.

Example O. The prosthetic cover of any of the preceding examples, wherein the first flexible end seal and the second flexible end seal are removably connected with the hollow body.

Example P. The prosthetic cover of any of the preceding examples, wherein the hollow body comprises a profile approximating a natural contour of an ankle and shin.

Example Q. A prosthesis, comprising: a prosthetic support element; and the prosthetic cover of any of examples A-P, wherein the prosthetic cover is connected with the prosthetic support element by passing the prosthetic support element through the hollow body of the prosthetic cover and through each one of the first flexible end seal and second flexible end seal such that the first flexible end seal and second flexible end seal support the prosthetic cover with respect to the prosthetic support element.

Example R. The prosthesis of example Q, wherein the prosthetic support element comprises an endoskeletal prosthetic support pylon.

Example S. The prosthesis of example Q or example R, further comprising a socket connected with the prosthetic support element and configured to receive an extremity of a user.

Example T. A method of installing a prosthetic cover with a prosthetic support element, the method comprising: passing the prosthetic support element through the prosthetic cover of any of examples A-P; connecting the first flexible end seal of the prosthetic cover with the prosthetic support element by deforming the first end cap around the prosthetic support element; connecting the first flexible end seal with the first end of the hollow body; connecting the second flexible end seal of the prosthetic cover with the prosthetic support element by deforming the second end cap around the prosthetic support element; and connecting the second flexible end seal with the second end of the hollow body such that the hollow body of the prosthetic cover is supported by the first and second flexible end seals.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A prosthetic cover for a prosthetic support element, the prosthetic cover comprising:
    a hollow body with a first end and a second end, wherein the hollow body is sized to fit around a support element of a prosthesis;
    a first flexible end seal configured to attach with the hollow body at the first end, and further comprising a first flexible opening therethrough that is sized to receive the prosthetic support element, wherein the first flexible end seal comprises a substantially ring-shaped first flexible gasket element connected with the first end of the hollow body, and a first end cap connected to the first flexible gasket element and configured to press the first flexible gasket element onto the first end of the hollow body; and
    a second flexible end seal configured to attach with the hollow body at the second end and further comprising a second flexible opening therethrough that is sized to receive the prosthetic support element, wherein the second flexible end seal comprises a substantially ring-shaped second flexible gasket element connected with the second end of the hollow body, and a second end cap connected to the second flexible gasket element and configured to press the second flexible gasket element onto the second end of the hollow body, and wherein each of the first and second flexible end seals is configured to connect the prosthetic cover with the prosthetic support element by deforming about the prosthetic support element when the prosthetic cover is installed around the prosthetic support element.

2. The prosthetic cover of claim 1, wherein each one of the first flexible end seal and second flexible end seal forms a respective fluid-tight connection between the hollow body and the support element when the prosthetic cover is installed around the support element.

3. The prosthetic cover of claim 1, wherein the hollow body comprises a polymer shell having at least one of a substantially cylindrical shape, hour-glass shape, or bulbous shape.

4. The prosthetic cover of claim 1, wherein the hollow body comprises a ribbed or wavy shape that is operable to allow the hollow body to deform longitudinally.

5. The prosthetic cover of claim 1, wherein each one of the first flexible end seal and second flexible end seal comprises a flexible silicone.

6. The prosthetic cover of claim 1, further comprising:
    a first locking band encircling the first flexible end seal and configured to secure the first flexible end seal to the hollow body; and
    a second locking band encircling the second flexible end seal and configured to secure the second flexible end seal to the hollow body.

7. The prosthetic cover of claim 1, wherein the prosthetic cover is rotationally symmetrical.

8. The prosthetic cover of claim 1, wherein the hollow body comprises a UV-resistant material.

9. The prosthetic cover of claim 1, wherein the first flexible end seal and the second flexible end seal comprise a vibration dampening material.

10. The prosthetic cover of claim 1, wherein:
    the first flexible end seal and the second flexible end seal are connected with the hollow body by a watertight seal; and
    the first flexible end seal and the second flexible end seal are configured to form a watertight seal with the prosthetic support element when the prosthetic cover is installed around the prosthetic support element.

11. The prosthetic cover of claim 1, wherein the first flexible end seal and the second flexible end seal are removably connected with the hollow body.

12. The prosthetic cover of claim 1, wherein the hollow body comprises a profile approximating a natural contour of an ankle and shin.

13. A prosthetic cover for a prosthetic support element, the prosthetic cover comprising:
    a hollow body with a first end and a second end, wherein the hollow body is sized to fit around a support element of a prosthesis, wherein the hollow body comprises a main body and a removable panel that is removably connected with the main body in a lateral direction with respect to the main body;
    a first flexible end seal configured to attach with the hollow body at the first end, and further comprising a first flexible opening therethrough that is sized to receive the prosthetic support element; and
    a second flexible end seal configured to attach with the hollow body at the second end and further comprising a second flexible opening therethrough that is sized to receive the prosthetic support element, wherein each of the first and second flexible end seals is configured to connect the prosthetic cover with the prosthetic support element by deforming about the prosthetic support element when the prosthetic cover is installed around the prosthetic support element.

14. A prosthetic cover for a prosthetic support element, the prosthetic cover comprising:
    a hollow body with a first end and a second end, wherein the hollow body is sized to fit around a support element of a prosthesis, wherein the hollow body comprises an upper body portion and a lower body portion connected with the upper body portion by a sliding fit configured to allow the hollow body to vary in length;
    a first flexible end seal configured to attach with the hollow body at the first end, and further comprising a first flexible opening therethrough that is sized to receive the prosthetic support element; and
    a second flexible end seal configured to attach with the hollow body at the second end and further comprising a second flexible opening therethrough that is sized to receive the prosthetic support element, wherein each of the first and second flexible end seals is configured to connect the prosthetic cover with the prosthetic support element by deforming about the prosthetic support element when the prosthetic cover is installed around the prosthetic support element.

15. A prosthetic cover for a prosthetic support element, the prosthetic cover comprising:
- a hollow body with a first end and a second end, wherein the hollow body is sized to fit around a support element of a prosthesis;
- a first flexible end seal configured to attach with the hollow body at the first end, and further comprising a first flexible opening therethrough that is sized to receive the prosthetic support element;
- a second flexible end seal configured to attach with the hollow body at the second end and further comprising a second flexible opening therethrough that is sized to receive the prosthetic support element, wherein each of the first and second flexible end seals is configured to connect the prosthetic cover with the prosthetic support element by deforming about the prosthetic support element when the prosthetic cover is installed around the prosthetic support element; and
- a pocket enclosure defined in an external surface of the hollow body and an external closure configured to enclose the pocket enclosure that can be opened and closed by a user.

16. A prosthesis, comprising:
- a prosthetic support element; and
- the prosthetic cover of claim 1, wherein the prosthetic cover is connected with the prosthetic support element by passing the prosthetic support element through the hollow body of the prosthetic cover and through each one of the first flexible end seal and second flexible end seal such that the first flexible end seal and second flexible end seal support the prosthetic cover with respect to the prosthetic support element.

17. The prosthesis of claim 16, wherein the prosthetic support element comprises an endoskeletal prosthetic support pylon.

18. The prosthesis of claim 16, further comprising a socket connected with the prosthetic support element and configured to receive an extremity of a user.

19. A method of attaching a prosthetic cover to a prosthetic support element, the method comprising:
- providing the prosthetic cover of claim 1;
- passing the prosthetic support element through the prosthetic cover;
- connecting the first flexible end seal of the prosthetic cover with the prosthetic support element by deforming the first end cap around the prosthetic support element;
- connecting the first flexible end seal with the first end of the hollow body;
- connecting the second flexible end seal of the prosthetic cover with the prosthetic support element by deforming the second end cap around the prosthetic support element; and
- connecting the second flexible end seal with the second end of the hollow body
- such that the hollow body of the prosthetic cover is supported by the first and second flexible end seals.

* * * * *